United States Patent [19]
Ruoslahti et al.

[11] Patent Number: 6,046,162
[45] Date of Patent: *Apr. 4, 2000

[54] SUPPRESSION OF CELL PROLIFERATION BY DECORIN

[75] Inventors: Erkki I. Ruoslahti, Rancho Santa Fe; Yu Yamaguchi, San Diego, both of Calif.

[73] Assignee: La Jolla Cancer Research Foundation, La Jolla, Calif.

[*] Notice: This patent is subject to a terminal disclaimer.

[21] Appl. No.: 08/458,830

[22] Filed: Jun. 2, 1995

Related U.S. Application Data

[63] Continuation of application No. 07/645,339, Jan. 22, 1991, Pat. No. 5,726,149, which is a continuation of application No. 07/212,702, Jun. 28, 1988, abandoned.

[51] Int. Cl.[7] .......................... A61K 38/02; A61K 38/16; A61K 38/39
[52] U.S. Cl. .................................. 514/8; 514/2; 530/350; 530/395
[58] Field of Search ............................ 435/240.2, 240.23, 435/172.3; 514/82; 530/350, 395; 935/66, 70

[56] References Cited

U.S. PATENT DOCUMENTS 5,583,103 12/1996 Ruoslahti et al. ........................ 514/8

FOREIGN PATENT DOCUMENTS

282317 A2 9/1988 European Pat. Off. .

OTHER PUBLICATIONS

Bassols and Massague, "Transforming Growth Factor Beta Regulates the Expression and Structure of Extracellular Matrix Chondroitin/Dermatan Sulfate Proteoglycans", *J. Biol. Chem*, 263:3039–3045 (1988).
Brennan et al., "Effect of a Proteoglycan Produced by Rat Tumor Cells on Their Adhesion to Fibronectin–Collagen Substrata", *Cancer Research*, 43:4302–4307 (1983).
Castellot et al., "Inhibition of Vascular Smooth Muscle Cell Growth by Endothelial Cell Derived Heparin", *J. Biol. Chem*, 257:11256–11260 (1982).
Castellot et al., "Glomerular Endothelial Cells Secrete a Heparin like Inhibitor and a Peptide Stimulator of Mesangial Cell Proliferation", *Am. J. Pathol.*, 125:493–500 (1986).
Cheifetz et al., "The Transforming Growth Factor–Beta System, a Complex Pattern of Cross–reactive Ligand and Receptors", *Cell*, 48:409–415 (1987).
Day et al., "Molecular Cloning and Sequence Analysis of the cDNA for Small Proteoglycan II of Bovine Bone", *Biochem. J.*, 248:801–805 (1987).
Fritze et al., "An Antiproliferative Heparin Sulfate Species Produced by Postconfluent Smooth Muscle Cells", *J. Cell Biol.*, 100:1041–1049 (1985).
Harper et al., *Kidney International*, 26:875–880 (1984).

Ishiara et al., "Involvement of Phosphatidylinositol and Insulin in the Coordinate Regulation of Proteoheparan Sulfate Metabolism and Heptocycle Growth", *J. Biol. Chem.*, 262:1708–1716 (1987).
Kresse et al., "Glycosaminoglycan–free Small Proteoglycan Core Protein Secreted by Fibroblasts from a Patient with a Snydrome Resembling Progeroid", *Am. J. Hum. Genet.*, 41 (1987).
Massague and Like, "Cellular Receptors for Type Beta Transforming Growth Factor", *J. Biol. Chem.*, 260:2636–2645 (1985).
Patthy, L., "Detecting Homology of Distantly Related Protein with Consensus Sequences", *J. Mol. Biol.*, 198:567–577 (1987).
Pearson et al., "The $NH_2$–terminal Amino Acid Sequence of Bovine Skin Proteodermatan Sulfate", *J. Biological Chemistry*, 258:15101–15104 (1983).
Ruoslahti, E., "Structure and Biology of Proteoglycans", *Annual Reviews of Cell Biology*, 4:229–255 (1988).
Segarini and Seyedin, "The High Molecular Weight Receptor to Transforming Growth Factor–Beta Contains Glycosaminoglycan Chains", *J. Biol. Chem.*, 263:8366–8370 (1988).
Vogel et al., "Specific Inhibition of Type I and Type II Collagen Fibrilogenesis by the Small Proteoglycan of Tendon", *Biochem J.*, 223:587–589 (1984).
Yamaguchi et al., "Expression of Human Proteoglycan in Chinese Hamster Ovary Cells Inhibits Cell Proliferation", *Nature*, 336:244–246 (1988).
Brennan J Biol Chem. 259: 13742–50 (1984).
Krusius Pnas 83:7683–7687 (1926).
Border Nature 360: 361–364 (1992).
Dermer Biotechnology 12: 320 (1994).
Border N. Eng. J. Med. 331:1286–1292 (1994).
Border J. Clin. Invest. 90: 1–7 (1992).
Massague Cancer Surveys 12: 81–103 (1992).
Webster's II New Riverside Dictionary p. 770 only, Houghton Mifflin Co 1988.
Freshney Culture of Animal Cells: A Manual of Basic Technique Alan R. Liss Inc N.Y. 1983 p. 125–128 only.
Takeuchi et al. J Biol Chem. 269: 32634–32638 (1994).
Hausser et al FEBS Letters 353: 243–245 (1994).
Santra et al. Pnas 92: 7016–7020 (1995).
Wood et al. Biochemistry A Problems Approach 1981 p. 14.5 only Benjamin/Cummings Publishing Co Menlo Park CA.
Santra et al. J. Clin Invest. 100:149–157 (1997).
Giri et al. Biochemical Pharmacology 54:1205–1216 (1997).
Yamaguchi et al. Nature 346: 281–284 (1990).
Stander et al. Gene Therapy 5: 1187–1194 (1998).

*Primary Examiner*—Christina Y. Chan
*Assistant Examiner*—Phillip Gambel
*Attorney, Agent, or Firm*—Campbell & Flores LLP

[57] ABSTRACT

A method of suppressing cell proliferation of a mammalian cell by contacting the cell with decorin.

3 Claims, 10 Drawing Sheets

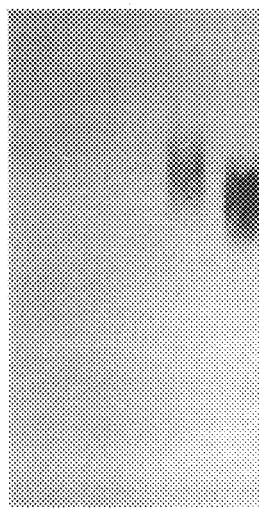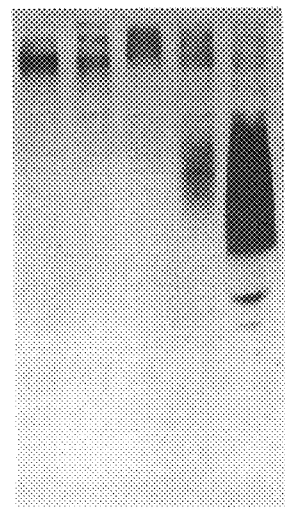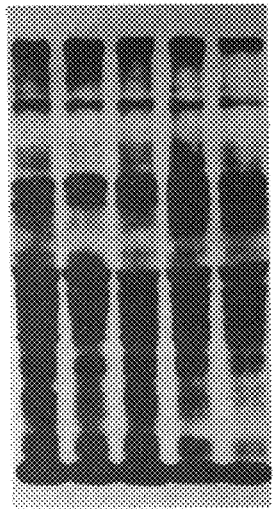

```
                                                                                                                   -91
GAA TTC CGG TTA CGT CTG CCC CCC GGT CGC AAA TTC CCG GAT TAA AAG GTT CCC TGG TTG TGA AAA TAC ATG AGA TAA ATC
                                                                                                                   -1
ATG AAG GCC ACT ATC CTC CTT CTG CTT GCA CAA GTT TCC TGG GCT GGA CCG TTT CAA CAG AGA GGC TTA TTT GAC TTT ATG CTA GAA
Met Lys Ala Thr Ile Leu Leu Leu Leu Ala Gln Val Ser Trp Ala Gly Pro Phe Gln Gln Arg Gly Leu Phe Asp Phe Met Leu Glu
-30                            -20                  -10
                                                                                                                   90
GAT GAG GCT TCT GGG ATA GGC CCA GAA GTT CCT GAT GAC CGC TCC CTA GGC CCA GTG TGC CCC TTC CGC TGT CAA TGC
Asp Glu Ala Ser Gly Ile Gly Pro Glu Val Pro Asp Asp Arg Ser Leu Gly Pro Val Cys Pro Phe Arg Cys Gln Cys
 1                  10                         20                         30
                                                                                                                   180
CAT CTT CGA GTC CAG TGT TCT GAT TTG GGT CTG GAC AAA GTG CCA AAG GAT CTT CCC CCT GAC ACA ACT CTG CTA GAC CTG CAA AAC
His Leu Arg Val Gln Cys Ser Asp Leu Gly Leu Asp Lys Val Pro Lys Asp Leu Pro Pro Asp Thr Thr Leu Leu Asp Leu Gln Asn
                    40                         50                         60
                                                                                                                   270
AAC AAA ATA ACC GAA ATC AAA GAT GGA GAC TTT AAG AAC CTT CAC GCA TTG CTT ATT CTT GTC AAC AAT AAA ATT AGC AAA GTT
Asn Lys Ile Thr Glu Ile Lys Asp Gly Asp Phe Lys Asn Leu His Ala Leu Leu Ile Leu Val Asn Asn Lys Ile Ser Lys Val
 61                 70                         80                         90
                                                                                                                   360
AGT CCT GGA GCA TTT ACA CCT TTG GTG AAG TTG GAA CGA CTT TAT CTG TCC AAG AAT CAG CTG AAG GAA TTG CCA GAA AAA ATG CCC AAA
Ser Pro Gly Ala Phe Thr Pro Leu Val Lys Leu Glu Arg Leu Tyr Leu Ser Lys Asn Gln Leu Lys Glu Leu Pro Glu Lys Met Pro Lys
 91                   100                        110                        120
                                                                                                                   450
ACT CTT CAG GAG CTG CGT GCC CAT CTG AAT GAG CGA AAT GTT ACT TTC AAT GGA CTG AAC CAG ATG ATT GTC ATA GAA
Thr Leu Gln Glu Leu Arg Ala His Leu Asn Glu Arg Lys Val Thr Phe Asn Gly Leu Asn Gln Met Ile Val Ile Glu
121                   130                        140
```

FIG. 8A

```
CTG GGC ACC AAT CCG CTG AAG AGC TCA GGA ATT GAA AAT GGG GCT TTC CAG GGA ATG AAG AAG CTC TCC TAC ATC CGC ATT GCT GAT ACC
Leu Gly Thr Asn Pro Leu Lys Ser Ser Gly Ile Glu Asn Gly Ala Phe Gln Gly Met Lys Lys Leu Ser Tyr Ile Arg Ile Ala Asp Thr
151                                         160                             170                                     540

AAT ATC ACC AGC ATT CCT CAA GGT CTT CCT CCC TCC CTT ACG GAA TTA CAT CTT GAT GGC AAC AAA ATC AGC AGA GTT GAT GCA GCT AGC
Asn Ile Thr Ser Ile Pro Gln Gly Leu Pro Pro Ser Leu Thr Glu Leu His Leu Asp Gly Asn Lys Ile Ser Arg Val Asp Ala Ala Ser
181                                         190                             200                                     630

CTG AAA GGA AAT AAT TTG GCT AAG TTG GGA TTG AGT TTC AAC AGC ATC TCT GCT GTT GAC AAT GGC TCT CTG GCC AAC ACG CCT CAT
Leu Lys Gly Asn Asn Leu Ala Lys Leu Gly Leu Ser Phe Asn Ser Ile Ser Ala Val Asp Asn Gly Ser Leu Ala Asn Thr Pro His
211                                         220                             230                                     720

CTG AGG GAG CTT CAC TTG GAC AAC AAC AAG CTT ACC AGA GTA CCT GGT GGG CTG GCA GAG CAT AAG TAC ATC CAG GTT TAC CTT CAT
Leu Arg Glu Leu His Leu Asp Asn Asn Lys Leu Thr Arg Val Pro Gly Gly Leu Ala Glu His Lys Tyr Ile Gln Val Tyr Leu His
241                                         250                             260                                     810

AAC AAT ATC TCT GTA GTT GGA TCA GAC TTC TGC CCA GGA CAC AAC ACC AAA AAG GCT TCT TAT TCG GGT GTG AGT CTT TTC
Asn Asn Ile Ser Val Val Gly Ser Asp Phe Cys Pro Gly His Asn Thr Lys Lys Ala Ser Tyr Ser Gly Val Ser Leu Phe
271                                         280                             290                                     900

AGC AAC CCG GTC CAG TAC TGG GAG ATA CAG CCA ACC TTC AGA TGT GTC TAC GTG CGC TCT GCC ATT CAA CTC GGA AAC TAT AAG TAA
Ser Asn Pro Val Gln Tyr Trp Glu Ile Gln Pro Thr Phe Arg Cys Val Tyr Val Arg Ser Ala Ile Gln Leu Gly Asn Tyr Lys ---
301                                         310                             320                                     990
```

FIG. 8B

```
TTC TCA AGA AAG CCC TCA TTT TTA TAA CCT GGC AAA ATC TTG TTA ATG TCA TTG CTA AAA AAT AAA TAA AAG CTA GAT ACT GGA AAC  1080
                                                                                                                   CTA
ACT GCA ATG TGG ATG TTT TAC CCA CAT GAC TTA TTA TGC ATG TTA TGA TCA GTT GAT TTT GAG AAA GCT CTA TGA GCT AGT  1170
                                                    A   AAG CAG TTC CAG AAG TAA TTG CCT ACA ATA AAA AGA AAT  AAC
                                                                                                             TTT
TGC ATG GTT TTT TGT TTA ATG TAA TAT AGG AGA CCC TTC ACA TTC CAA AAC ATT CTT ATT GTG AAT ATC TAA GTT  1260
GCC CAT TTT CAG AAT CAT CTT TTG AAG CTT GTT GAT ATA ACT AGA GAT ATT TCA CTA AAT GTA AAA            TGT
                                                                                                   TTT
GAA ACT AGG GCA TGA TAC AGT AAG GTG CAA AAT GTA AAT TTA CAG CTG TCA CGA AAT GAC CTC TAC AGA GTT TTA TGG AAT ACC  1350
GGA GTA ATA GTC AAT ATT TAG TAA GCC TAG AAC AAT TTA TCT AGG AAA AAA TAA CTT CAT GAG TAT TCT GTA TAC
                                                                                                   CAT
TAA CGT AGG CAG CTG CAA AAC CAC ACT GAG TTA CAG CTG TCA GCC CTC ATT CCT AAA TAA CTT GCC CAT ATC AGC CCT  1440
TGA GCA GTT AGC TCA TTT GAG ATA AAG TCA AAT GCC TAG CTC TGT AAT CCC CAT TAC TGG TAA AGC GGA ATT  ACT
                                                                                                 C
TCT GAA GTT CAA ATT AGT GCC TCG GAA ATG TAG AAT TTA TTA TTT GTC ATT TTT TTT TTA GCA TAG ATT GAG AAC AGT TGA ACT  1530
                                                                                                                CTT
AAA TCC TCA GAT GCC AGG GGT CTG CTC TAG CAT CAG TAA GTA TTT AGC AGA AAC TAA CTC CGT AAT GAA TGG AAT TC
```

FIG. 8C

SUPPRESSION OF CELL PROLIFERATION BY DECORIN

This application is a continuation of application Ser. No. 07/645,339, filed Jan. 22, 1991 now U.S. Pat. No. 5,726,149 which is a continuation of application Ser. No. 07/212,702, filed Jun. 28, 1988 now abandoned.

This invention relates to cell biology and more specifically to the control of cell proliferation.

Under normal circumstances, cell proliferation is a tightly controlled process; fast proliferation is needed during embryonal development and tissue regeneration, whereas the proliferation must be halted in the completed tissue. Cell proliferation appears to be controlled primarily by growth factors. Most of the known growth factors are stimulatory. Examples include epidermal growth factor, platelet-derived growth factor, various interleukins and colony-stimulating factors. A few negative regulators of cell proliferation are also known. Transforming growth factor beta is a multifunctional factor that inhibits the growth of some cell types, but can also stimulate proliferation. Other growth inhibitors include various interferons and a growth inhibitory role has also been ascribed to heparin, heparan sulfate and their fragments.

A less well understood mechanism of growth control relates to the close apposition of cells. Normal cells stop growing when they make contact with one another. This phenomenon, commonly known as contact inhibition of growth, is of obvious importance for the formation of orderly tissue structure.

A number of important pathological conditions depend on abnormal cell proliferation. The foremost of such conditions is, of course, cancer. Other diseases with a proliferative component include rheumatoid arthritis with its overgrowth of the synovial tissue, glomerulonephritis, in which the mesangial cells proliferate, and atherosclerosis, in which the abnormally proliferating cells are smooth muscle cells.

It is obvious from these examples that there is a great need to develop new methods for controlling cell proliferation. The present invention addresses this need and provides other related advantages as well.

SUMMARY OF THE INVENTION

The present invention relates to the proteoglycan Decorin (also known as PG-II or PG-40). The invention provides cells transfected with and expressing the gene coding for Decorin, and recombinant Decorin produced thereby. Spent culture media from such transfected cell cultures can be used to suppress the proliferation of either normal or abnormal cells. Moreover, purified Decorin can be used to suppress cell proliferation.

BRIEF DESCRIPTION OF THE DRAWINGS

FIG. 1 shows the expression of Decorin in unamplified and amplified transfectants.

FIG. 8 shows the nucleotide and deduced amino acid sequence of the decorin set forth in FIG. 2 of Krusius and Ruoslahti, Proc. Natl. Acad. Sci. USA, 83:7683; Nucleotide and amino acid residues are numbered from the amino terminus of the mature core protein. Nucleotides upstream from the amino terminus and amino acids in the signal and propeptide sequences are indicated by negative numbers. Signal and propeptide sequences are shown underlined (thin line) and the possible signal-peptidase cleavage site is indicated by an arrow. Potential glycosylation sites for N-linked glycans and glycosaminoglycans are shown by solid and open triangles, respectively. Serine at position 4 is known to carry a glycosaminoglycan. A 48-residue homologous sequence present twice in the core protein is shown underlined (bold line). The alternative 3' flanking sequence contained in clone 3C (lower line) is shown below the sequence of clone 5E (upper line) starting at base 1122 where the sequences diverge. Possible polyadenylylation signal sequences are underlined.

DETAILED DESCRIPTION OF THE INVENTION

Figure 2:
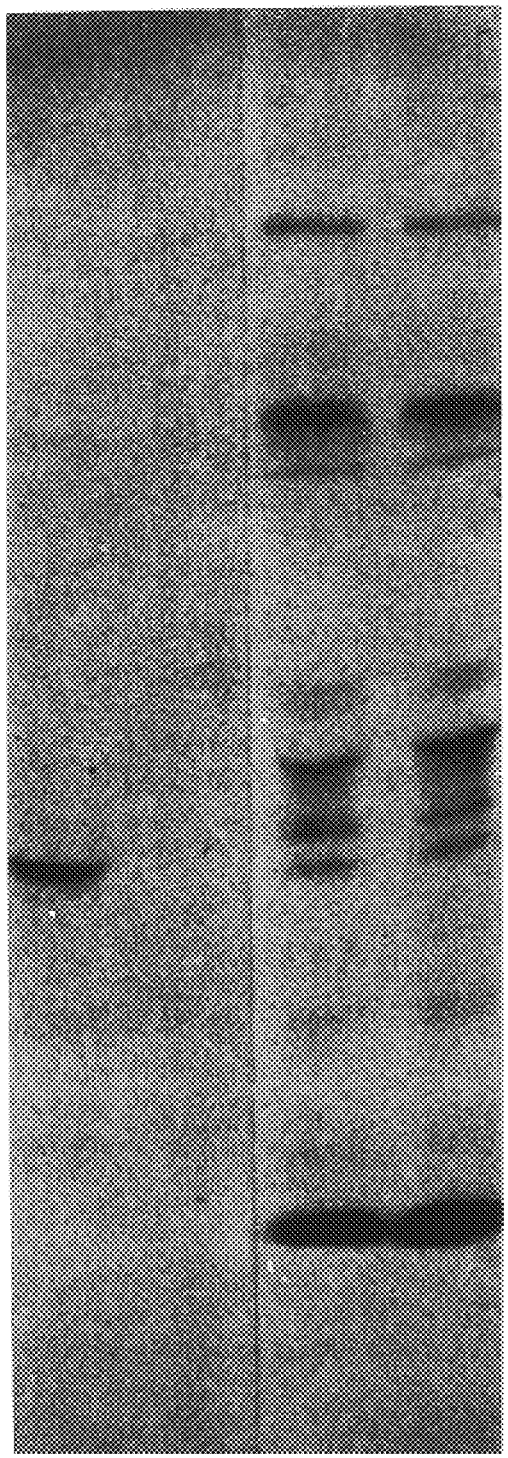
FIG. 2 is a radiogram showing the expression of Decorin core protein in CHO cells.
Figure 3A:
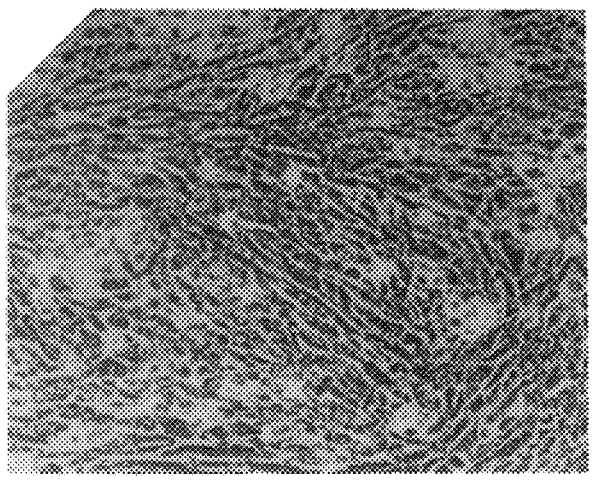
FIG. 3 shows morphological changes caused by expression of Decorin in CHO cells.
Figure 3B:
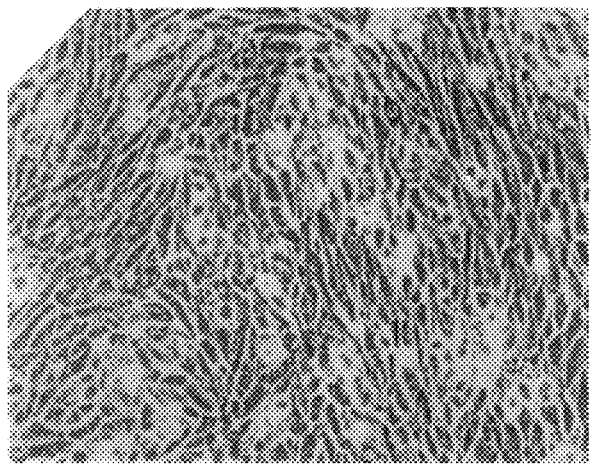
Figure 3C:
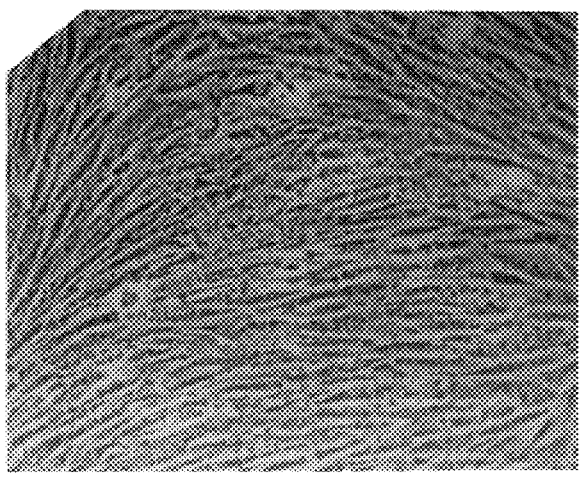
Figure 3D:
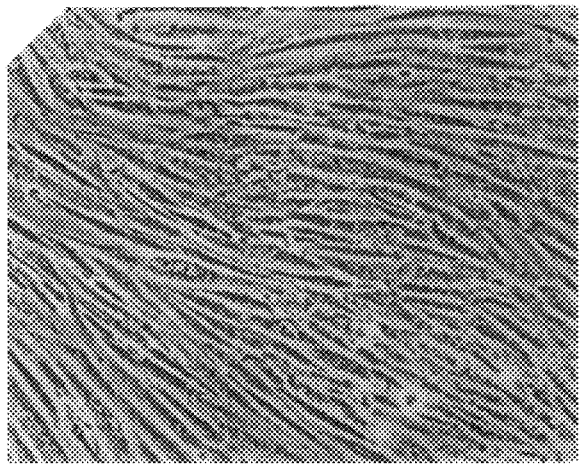
Figure 4:
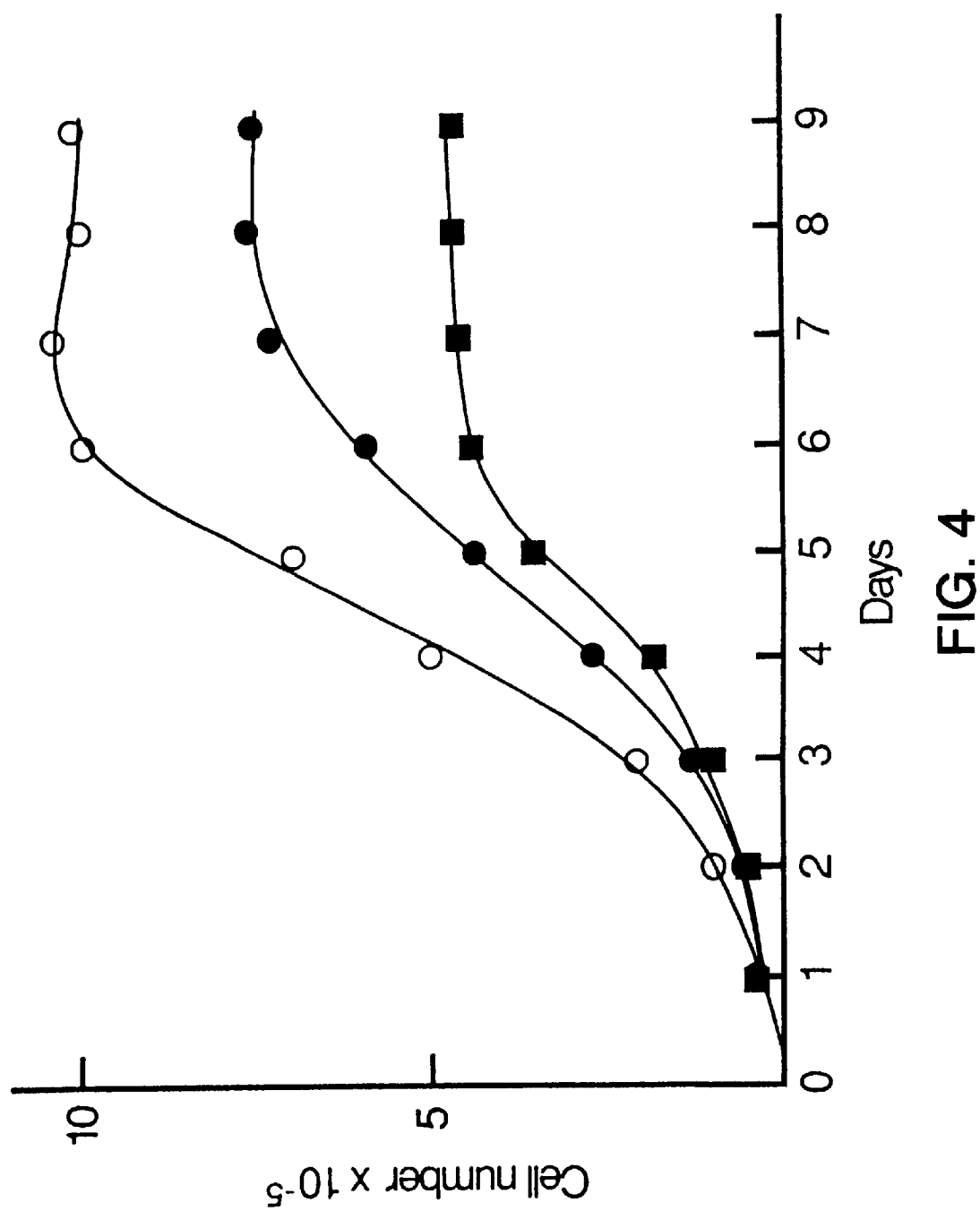
FIG. 4 is a graph showing the growth of Decorin-expressing and control CHO cells in culture.

This invention stems from work performed to explore the functions of a proteoglycan, Decorin. Proteoglycans are proteins that carry one or more glycosaminoglycan chains. The known proteoglycans carry out a variety of functions and are found in a variety of cellular locations. Many of them, however, are components of extracellular matrix, where they participate in the assembly of cells to the matrix and affect the attachment of cells to the matrix.

Decorin, also known as PG-II or PG-40, is a small proteoglycan produced by fibroblasts. Its core protein has a molecular weight of about 40,000 daltons. The core has been sequenced (Krusius and Ruoslahti, Proc. Natl. Acad. Sci. USA 83:7683 (1986); Day et al. Biochem. J. 248:801 (1987), both of which are incorporated herein by reference) and it is known to carry a single glycosaminoglycan chain of a chondroitin sulfate/dermatan sulfate type (Pearson, et al., J. Biol. Chem. 258:15101 (1983), which is incorporated herein by reference). The only previously known function for Decorin is its binding to type I and type II collagen and the effect it has on the fibril formation by this collagen (Vogel, et al., Biochem. J. 223:587 (1984)).

A molecular biological study of Decorin has now led to unexpected observations on its role in the control of cell proliferation, and these observations form the basis of this invention.

Decorin cDNA is transfected into cells, such as Chinese hamster ovary (CHO) cells, preferably those which are dihydrofolate reductase (dhfr)-negative, although other cells such as 3T3 and COS cells can also be used. Such transfection is accomplished by methods well-known in the art. The transfected cells are then grown in culture.

Chinese hamster ovary (CHO) cells into which human Decorin cDNA was transfected and which express the proteoglycan from this cDNA appear more adhesive to the substratum than the original cells. Moreover, the growth of the cells that expressed Decorin from the cDNA was suppressed and they grew to a lower saturation density than the various control cells. These controls included cells transfected with a construct expressing the core protein of Decorin and amplified to the same degree as the Decorin expressing cells. These cells were similar to the original CHO cells. The magnitude of the growth and adhesion changes was proportional to the amount of Decorin produced.

Moreover, changes in the adhesion and the saturation density could be reproduced with the spent culture media of the cells expressing the recombinant Decorin and with the Decorin isolated and purified from such culture media. These findings indicate that Decorin plays a previously unsuspected role in the control of cell proliferation, and that it can be used to modulate cell proliferation. The effect seen with oncogene-transformed 3T3 cells suggests that this invention may be useful in the treatment of proliferative diseases.

As used herein "Decorin" referes to a proteoglycan having the structural characteristics attributed to it in Krusius and Ruoslahti, supra, and which suppresses cell proliferation as determined by the method of Example III. Human fibroblast Decorin has substantially the amino acid sequence presented in Krusius and Ruoslahti supra, FIG. 2, which is incorporated herein by reference. The Decorin set forth in FIG. 2 of Krusius and Ruoslahti, supra, comprises the mature core protein set forth as amino acids 1–329 of FIG. 8 set forth herein. "Decorin" refers both to the native composition and to modifications thereof which retain the functional characteristics.

The recombinant Decorin of the invention has a structure corresponding substantially to that of the native proteoglycan. It is understood however that limited modifications may be made however without destroying the Decorin activity.

EXAMPLE I

EXPRESSION OF DECORIN AND DECORIN CORE PROTEIN

The 1.8 kb full-length Decorin cDNA described in Krusius and Ruoslahti, Proc. Natl. Acad. Sci. USA 83:7683 (1986), which is incorporated herein by reference, was used for the construction of Decorin expression vectors. For the expression of Decorin core protein, a mutagenized cDNA in which the fourth codon, TCT coding for serine, was changed to ACT coding for threonine was engineered by site-directed mutagenesis according to the method of Kunkel, Proc. Natl. Acad. Sci USA 82:488 (1985), which is incorporated herein by reference. The mammalian expression vectors pSV2-Decorin and pSV2-Decorin/CP (core protein) were constructed by ligating the Decorin cDNA or the mutagenized Decorin cDNA into 3.4 kb HindIII—Bam HI fragment of pSV2 (Mulligan and Berg, Science 209:1423 (1980) which is incorporated herein by reference), respectively. Dihydrofolate reductase (dhfr)-negative CHO cells (CHO-DG44) were cotransfected with pSV2-Decorin or pSV2-Decorin/CP and pSV2dhfr by the calcium phosphate coprecipitation method. The transfected cells were cultured in nucleoside-minus alpha-modified minimal essential medium (α-MEM, GIBCO, Long Island) supplemented with 9% dialyzed fetal calf serum, 2 mM glutamine, 100 units/ml penicillin and 100 µg/ml streptomycin. Colonies arising from transfected cells were picked using cloning cylinders, expanded and checked for the expression of Decorin by immunoprecipitation from $^{35}SO_4$-labeled culture supernatants. Clones expressing a substantial amount of Decorin were then subjected to gene amplification by stepwise increasing concentration of methotrexate (MTX, Kaufman and Sharp, J. Mol. Biol. 159:601 (1982) which is incorporated herein by reference) up to 0.64 µM. All the amplified cell lines were cloned either by limiting dilution or by picking single MTX resistant colonies. Stock cultures of these established cell lines were kept in MTX-containing medium. Before use in experiments, cells were subcultured in MTX-minus medium from stock cultures and passed at least once in this medium to eliminate the possible MTX effects. Controls were transfected only with pSV2dhfr and treated exactly as experimental cells thereafter. Metabolic labeling of the cells with $^{35}SO_4$ or $^3H$-leucine and immunoprecipitation was performed as described Brennan et al., J. Biol. Chem 259:13742 (1984), which in incorporated herein by reference.

FIG. 1 shows the expression of Decorin in unamplified and amplified transfectants, by using fluorography of SDS-7%-polyacrylamide gel electrophoresis under reducing conditions. (A) $^{35}SO_4$-labeled culture supernatants immunoprecipitated with rabbit antipeptide antiserum prepared against the NH$_2$-terminus of human Decorin (Krusius and Ruoslahti, supra.). (B) Total $^{35}SO_4$-labeled products secreted into culture medium. (C) Total $^3H$-leucine labeled products secreted into culture medium. Lane 1: control transfectant A, an unamplified clone transfected with pSV2dhfr; lane 2: control transfectant C, a clone amplified to 0.64λ M MTX resistance from control transfectant A; lane 3: clone 1, an unamplified primary transfectant expressing 0.2 pg/cell/day of Decorin; lane 4: clone 31, a clone amplified to 0.32 λ M MTX resistance and expressing 4 pg/cell/day of Decorin; lane 5: clone 61, a clone amplified to 0.64λ M MTX resistance and expressing 25 pg/cell/day of Decorin.

FIG. 2 shows expression of Decorin core protein in CHO cells. Lanes 1 and 2: $^3H$-leucine-labeled culture supernatants were immunoprecipitated as described in FIG. 1. Lanes 3 and 4: Total $^3H$-leucine-labeled products secreted into culture medium. Lanes 1 and 3: CHO cells transfected with pSV2-Decorin/CP. Lanes 2 and 4: Control CHO cells transfected with pSV2dhfr.

EXAMPLE II

QUANTITATION OF CELL SPREADING AND SATURATION DENSITY

The cell lines of Example I were plated in 24 well plates in MTX-minus culture medium at a density of 3×10$^5$ cells per well. After 24 hours, medium was replaced (0.3 ml per well) and cells were incubated another 24 hours. Concentration of Decorin in these culture supernatants was determined by competitive ELISA (Engvall, Meth. Enzymol. 70:419 (1980) which is incorporated herein by reference). Briefly, a mixture of culture supernatant and rabbit antipeptide antibody against Decorin was incubated in the wells of microtiter plates coated with Decorin purified from human fetal membranes (Brennan et al., supra.). The amount of antibody bound to the wells was determined by alkaline-phosphatase-conjugated goat anti-rabbit IgG as a second antibody. Various concentrations of purified Decorin were used to generate a standard curve. The cells were counted by hemocytometer at the end of the 24 hour incubation.

As shown in Table I, cells transfected with the Decorin gene exhibited a larger area of spreading than did control cells. Where Decorin expression was amplified, area of spreading increased with increasing expression.

Also shown in Table I are the saturation densities of the Decorin-expressing and control cells. In order to determine the saturation densities, cells (1.2×10$^5$) were plated in a 60 mm culture dish in MTX-minus culture medium. After 6 hours, cells were fixed with 3% paraformaldehyde and stained with toluidine blue. Quantitative evaluation of spreading was performed by measuring the surface area of the cells with a surface integration program of an image analyzer (Olympus). Nonspread cells were excluded from the measurement. The mean and standard deviation of values from 50 cells are shown.

TABLE I

PRODUCTION OF DECORIN AND SPREADING OF TRANSFECTANTS

| Clone | Transfection | MTX Resistance ($\mu$M) | Decorin Prod. ($\mu$g per $10^6$ cells/day) | Spread Area ($\mu M^2$/cell) | Saturation Density ($\times 10^{-5}$) |
|---|---|---|---|---|---|
| control line A | pSV2dhfr | 0 | 0 | 2725 ± 627 | 10.8 ± 1.2 |
| control line B | pSV2dhfr | 0.32 | 0 | 2585 ± 693 | 10.4 ± 2.5 |
| control line C | pSV2dhfr | 0.64 | 0 | 2659 ± 586 | 10.6 ± 1.8 |
| clone 1 | pSV2-decorin + pSV2dhfr | 0 | 0.2 | 3368 ± 842 | 9.9 ± 1.6 |
| clone 31 | pSV2-decorin + pSV2dhfr | 0.32 | 4 | 4759 ± 898 | 7.3 ± 0.2 |
| clone 33 | pSV2-decorin + pSV2dhfr | 0.32 | 11 | 5554 ± 1002 | 5.2 ± 0.2 |
| clone 66 | pSV2-decorin + pSV2dhfr | 0.64 | 14 | 5482 ± 1382 | 4.9 ± 0.3 |
| clone 61 | pSV2-decorin + psV2dhfr | 0.64 | 25 | 6472 ± 1147 | 4.4 ± 0.4 |

EXAMPLE III

ANALYSIS OF THE EFFECT OF SPENT CULTURE MEDIA

The effect of spent culture media on the morphology of CHO cells and Harvey ras gene-transformed NIH 3T3 cells was determined by plating CHO cells in 35 mm dishes at a density of $2\times10^5$ cells/dish in two-day spent media from clone 61 containing approximately 20 $\mu$g/ml of Decorin and in similar media from control cell line C containing no Decorin and cultured, the cell lines being those described in Example I.

Figure 5:
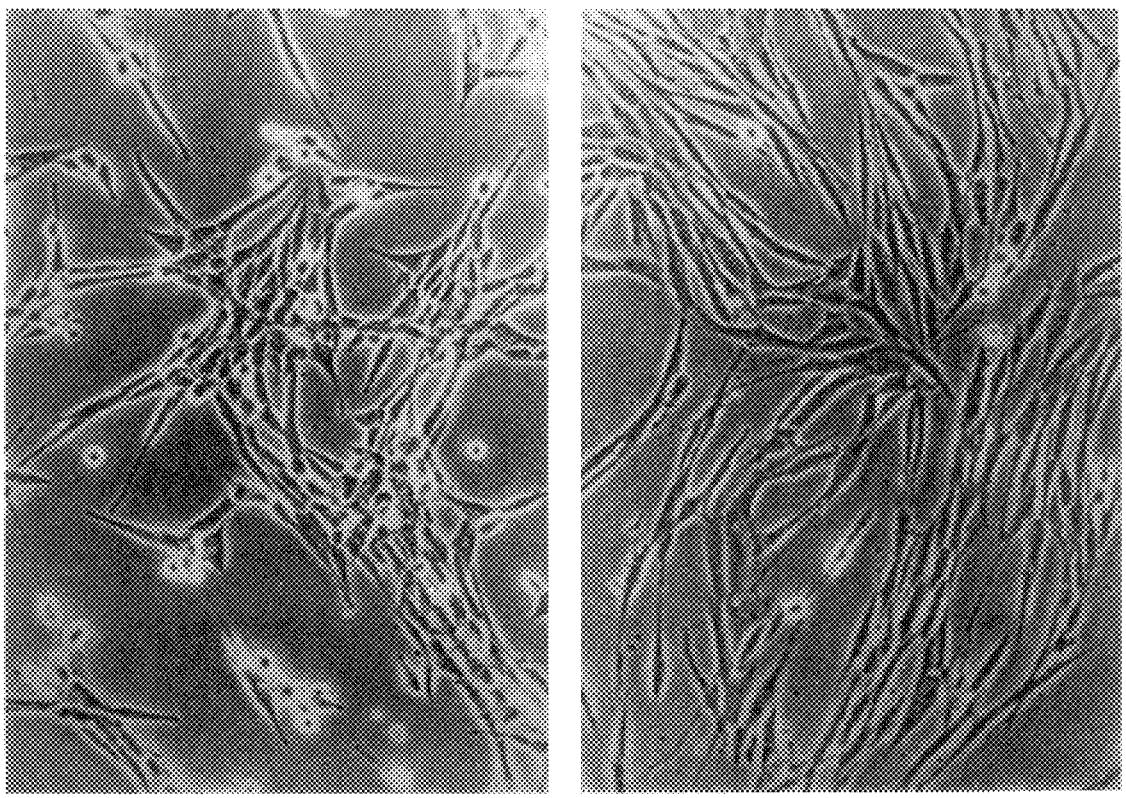
FIG. 5 is a photomicrograph showing the effect of spent culture media on the morphology of CHO cells.
Figure 6:
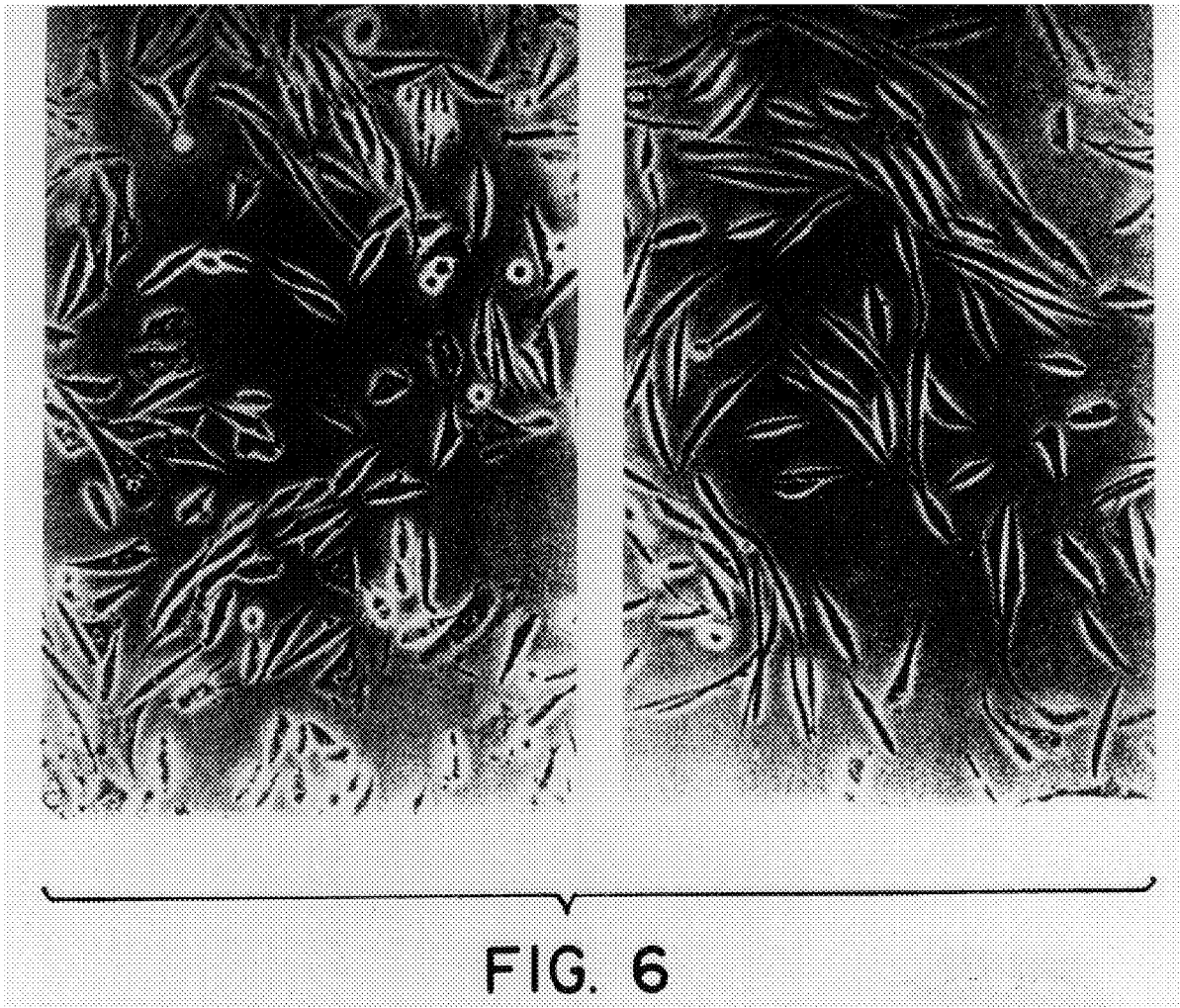
FIG. 6 is a photomicrograph showing the effect of spent culture media on the morphology of Harvey ras gene-transformed NIH 3T3 cells.

FIG. 5 shows the morphology of the CHO cells after this treatment and FIG. 6 shows the morphology of the treated oncogen-transformed 3T3 cells. As can be seen, the spent culture medium from the Decorin-expressing cell line, clone 31, induced a morphology similar to that observed in the Decorin-expressing cells themselves. The oncogene-transformed 3T3 cells treated in this manner assume a morphology closely similar to that of normal cells. This morphology is often referred to as "contact inhibited morphology" and it is considered to be indicative of normal growth control. In accordance with this phenomenon, fewer cells were seen in these cultures compared to the control-media treated cultures. These results indicate that the culture media from the cell lines expressing Decorin reproduces the morphological and growth inhibiting effects seen in the recombinant Decorin-expressing cells themselves.

EXAMPLE IV

PURIFICATION OF DECORIN FROM SPENT CULTURE MEDIA

Clone 61 cells were grown to 90% confluence in 8 175 $cm^2$ culture flasks in nucleoside minus $\alpha$-MEM supplemented with 9% dialyzed fetal calf serum, 2 mM glutamine, 100 units/ml penicillin and 100 $\mu$g/ml streptomycin. At 90% confluence culture media was changed to 25 ml per flask of nucleoside-free $\alpha$-MEM supplemented with 6% dialyzed fetal calf serum which had been passed through a DEAE Sepharose Fast Flow column (Pharmacia) equilibrated with 0.25 M NaCl in 0.05 M phosphate buffer, pH 7.4. Cells were cultured for 3 days, spent media was collected and immediately made to 0.5 mM phenylmethylsulfonyl fluoride, 1 $\mu$g/ml pepstatin, 0.04 mg/ml aprotinin and 5 mM EDTA.

Four hundred milliliters of the spent media were first passed through gelatin-Sepharose to remove fibronectin and materials which would bind to Sepharose. The flow-through fraction was then mixed with DEAE-Sepharose preequilibriated in 50 mM Tris/HCl, pH 7.4, plus 0.2 M NaCl and batch absorbed overnight at 4° C. with gentle mixing. The slurry was poured into a 1.6×24 cm column, washed extensively with 50 mM Tris/HCl, pH 7.4, containing 0.2 M NaCl and eluted with 0.2 M –0.8 M linear gradient of NaCl in 50 mM Tris/HCl, pH 7.4. Decorin concentration was determined by competitive ELISA as described above.

Figure 7:
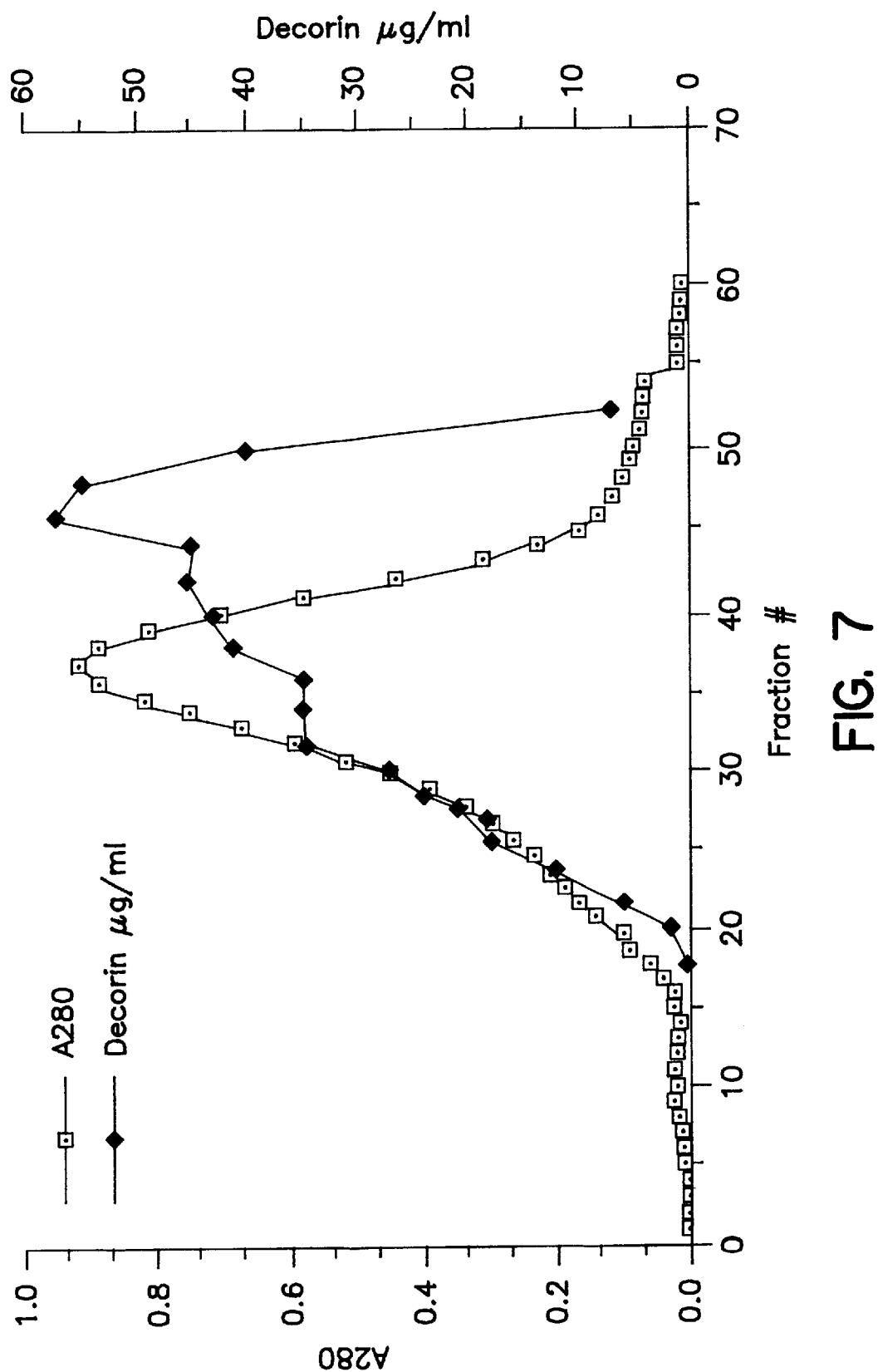
FIG. 7 shows the elution pattern from DEAE-Sepharose of spent culture media from Decorin-expressing cell line, clone 61.

FIG. 7 shows the elution pattern in DEAE-Sepharose Fast Flow. As can be seen, Decorin separates from the bulk of the protein present in the media and can be recovered in substantially pure form from the fractions showing the highest immune reactivity.

Although the invention has been described with reference to the presently-preferred embodiment, it should be understood that various modifications can be made without departing from the spirit of the invention. Accordingly, the invention is limited only by the following claims.

We claim:

1. A method of suppressing cell proliferation of a mammalian cell capable of being suppressed by decorin, comprising contacting said cell with decorin.

2. The method of claim 1, wherein said decorin comprises the mature core protein set forth as amino acids 1–329 of FIG. 8.

3. The method of claim 1, wherein said Decorin is produced by recombinant means.

* * * * *